United States Patent
Hotter et al.

(10) Patent No.: US 10,265,326 B2
(45) Date of Patent: Apr. 23, 2019

(54) FORM C OF AVIBACTAM SODIUM

(71) Applicant: Sandoz AG, Basel (CH)

(72) Inventors: Andreas Hotter, Kundl (AT); Verena Adamer, Kundl (AT); Hannes Lengauer, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 15/750,849

(22) PCT Filed: Aug. 9, 2016

(86) PCT No.: PCT/EP2016/068925
§ 371 (c)(1),
(2) Date: Feb. 7, 2018

(87) PCT Pub. No.: WO2017/025526
PCT Pub. Date: Feb. 16, 2017

(65) Prior Publication Data
US 2018/0193351 A1    Jul. 12, 2018

(30) Foreign Application Priority Data
Aug. 10, 2015 (EP) ..................... 15180413

(51) Int. Cl.
| | | |
|---|---|---|
| *C07D 471/04* | (2006.01) | |
| *A61K 31/551* | (2006.01) | |
| *A61K 31/439* | (2006.01) | |
| *A61P 31/04* | (2006.01) | |
| *B01D 9/00* | (2006.01) | |

(52) U.S. Cl.
CPC .......... *A61K 31/551* (2013.01); *A61K 31/439* (2013.01); *A61P 31/04* (2018.01); *B01D 9/0054* (2013.01); *C07D 471/04* (2013.01)

(58) Field of Classification Search
CPC ... C07D 471/04; C07D 471/08; A61K 31/439
See application file for complete search history.

(56) References Cited

U.S. PATENT DOCUMENTS 7,112,592 B2    9/2006 Lampilas et al.

FOREIGN PATENT DOCUMENTS

| CN | 106699756 A | 5/2017 |
|---|---|---|
| WO | 0210172 A1 | 2/2002 |
| WO | 2011042560 A1 | 4/2011 |
| WO | 2012172368 A1 | 12/2012 |
| WO | 2014135930 A1 | 9/2014 |

OTHER PUBLICATIONS

International Search Report and Written Opinion for PCT/EP2016/068925, dated Feb. 16, 2017, 10 pages.
Anonymous, New Drug Application (NDA) 206494: Submission Suppl-1: Labeling-Package Insert for AVYCAZ (ceftazidime and avibactam), (2015).
Database Chemcats, Chemical Abstracts Service, Columbus, Ohio, Feb. 23, 2015.
FDA, Dosage Forms and Strengths, https://www.accessdata.fda.gov/drugsatfda_docs/label/2015/206494s001lbl.pdf, Sep. 2, 2015, pp. 1-20.
International Search Report and Written Opinion for PCT/EP2017/071471, dated Dec. 18, 2017, 20 pages.

*Primary Examiner* — Deepak R Rao
(74) *Attorney, Agent, or Firm* — Luedeka Neely Group, P.C.

(57) ABSTRACT

The present invention relates to crystalline form C of avibactam sodium and to a process for its preparation. The invention also concerns a pharmaceutical composition comprising form C and one or more antibacterial agents, wherein at least one antibacterial agent is a beta-lactam antibiotic. The pharmaceutical composition of the present invention can be used as medicament, in particular for treatment and/or prevention of bacterial infections.

13 Claims, 4 Drawing Sheets

FORM C OF AVIBACTAM SODIUM

This application is a Section 371 national phase entry of PCT application of PCT/EP2016/068925, filed Aug. 9, 2016. This application also claims the benefit of the earlier filing dates of European patent application 15180413.5, filed Aug. 10, 2015, as well as European patent application 15187315.5, filed Sep. 29, 2015.

FIELD OF THE INVENTION

The present invention relates to crystalline form C of avibactam sodium and to a process for its preparation. The invention also concerns a pharmaceutical composition comprising form C and one or more antibacterial agents, wherein at least one antibacterial agent is a beta-lactam antibiotic. The pharmaceutical composition of the present invention can be used as medicament, in particular for treatment and/or prevention of bacterial infections.

BACKGROUND OF THE INVENTION

Avibactam sodium belongs to the class of non-beta-lactam beta-lactamase inhibitors and is intended to be used in conjunction with beta-lactam antibiotics for the treatment of bacterial infections. It protects beta-lactam antibiotics from degradation by beta lactamase enzymes and therefore maintains the antibacterial activity of beta-lactam antibiotics.

WO 02/10172 A1 describes the racemic sodium salt of trans-7-oxo-6-sulfooxy-1,6-diazabicyclo[3.2.1]octane-2-carboxamide in crystalline form and a method for its preparation.

However, it was found that only one enantiomer is active, which is the sodium salt of (1R,2S,5R)-7-oxo-6-sulfooxy-1,6-diazabicyclo[3.2.1]octane-2-carboxamide (international non-proprietary name: avibactam sodium) represented by chemical structure (I)

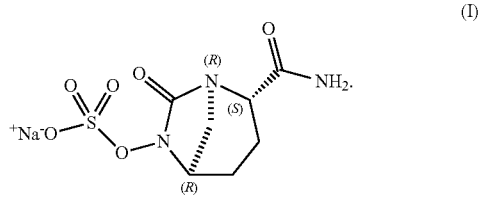

(I)

WO 2011/042560 A1 describes avibactam sodium crystalline forms A, B, D and E and mentions a mixture of at least one of these forms with a form C. It does however not contain any disclosure for the preparation of a form C or said mixtures.

WO 2014/135930 A1 discloses a crystalline form of avibactam sodium characterized by powder X-ray diffraction. According to the peak list provided on page 6 and the corresponding powder X-ray diffractogram of FIG. 1 this crystalline form can be assigned to a mixture of crystalline forms of avibactam sodium comprising at least form B and form D of WO 2011/042560 A1, while form C is not present.

It is well-known by the skilled person that upon temperature stress or under acidic or basic conditions hydrated forms often tend to hydrolyze. Hydrates are also prone to dehydration, for example, they readily lose their water when subjected to dry conditions and/or increased temperatures. For example, WO 2011/042560 A1 mentions that the avibactam sodium dihydrate form E tends to lose water and to hydrolyze during long storage and at higher temperature (page 17, lines 1 to 2). It is further stated in the application that form E is particularly stable above relative humidities of about 70% (page 15, line 25), indicating that this hydrated form is only stable in the presence of moisture. In addition, it was found that form E dehydrates to the monohydrate form A at temperatures above about 60° C. and that form A upon further temperature stress dehydrates to the anhydrous form B. Such conversions of physical forms are critical as pharmaceutical processing and milling usually involves the evolution of heat. Hence, for pharmaceutical purposes anhydrous forms of avibactam sodium are preferred over hydrates.

Besides proper physical properties, the manufacturability of a solid form determines whether it is a feasible candidate for the preparation of a drug product. According to WO 2011/042560 A1 (page 16, lines 30 to 31) anhydrous form D was only obtained as very small crystals, making filtration difficult and slow and hence making it difficult to prepare form D. Thus, due to its limitations with regard to isolation, form D cannot be produced on an industrial scale. In addition, the robustness and reliability of a manufacturing process is a key criterion for physical form selection. WO 2011/042560 A1 (page 17, lines 8 to 14) for example mentions that anhydrous form B is difficult to prepare in the absence of seed crystals and only obtained in a very narrow range of water activity. The seed crystal preparation disclosed in the application (page 16, lines 22 to 26) seems not to be straightforward, let alone industrially applicable. Therefore, a reliable industrial production of anhydrous form B seems to be very challenging.

An objective of the present invention was therefore the provision of a crystalline form, preferably a crystalline anhydrous form of avibactam sodium which is polymorphically stable, i.e. which does not convert to any other physical form of avibactam sodium during pharmaceutical processing and/or upon storage. A further objective was the provision of avibactam sodium in a crystalline form, preferably in a crystalline anhydrous form which is polymorphically pure or essentially polymorphically pure, i.e. is free or essentially free of any other physical form of avibactam sodium. Further, it is an objective to provide a solid pharmaceutical composition comprising a crystalline form, preferably a crystalline anhydrous form of avibactam sodium, wherein the crystalline (anhydrous) form of avibactam sodium is polymorphically stable within the pharmaceutical composition and under various conditions, e.g. at ambient storage conditions. In addition, it is an objective to provide a solid pharmaceutical composition comprising a crystalline form, preferably a crystalline anhydrous form of avibactam sodium, wherein the crystalline (anhydrous) form of avibactam sodium is present in polymorphically pure form or essentially polymorphically pure form.

Finally, another objective of the present invention is the provision of a crystalline form, preferably a crystalline anhydrous form of avibactam sodium, which is reliably producible on an industrial scale in polymorphically or essentially polymorphically pure and/or stable form.

SUMMARY OF THE INVENTION

The present invention relates to anhydrous crystalline form C of avibactam sodium and to an industrially applicable, reliable and robust process for its preparation. Said form C is polymorphically stable under ambient conditions as well as under conditions occurring in the manufacturing of a solid pharmaceutical dosage form, e.g. a powder for injection. Moreover, form C as defined herein is from a physical form perspective stable upon storage within a solid pharmaceutical composition, e.g. a powder for injection, over shelf life. Hence, form C of the present invention does not convert to any other physical form of avibactam sodium during formulation and storage of a pharmaceutical composition. The present invention also relates to crystalline form C of avibactam sodium, which is polymorphically pure or essentially polymorphically pure, i.e. which is free or essentially free of any other physical forms, in particular free or essentially free of forms A, B, D and E of avibactam sodium as described in WO 2011/042560 A1 and to a process for preparing the same.

Surprisingly, avibactam sodium form C of the present invention was found to be physically stable against moisture and highly stable against temperature stress, which qualifies it to be used for the preparation of pharmaceutical products.

Therefore, the present invention also concerns a pharmaceutical composition comprising avibactam sodium form C as disclosed herein, preferably an effective and/or predetermined amount of avibactam sodium form C as disclosed herein.

The present invention also concerns a pharmaceutical composition comprising avibactam sodium, wherein said avibactam sodium is present as avibactam sodium form C as disclosed herein, wherein said pharmaceutical composition does not contain or is essentially free of any other physical form, e.g. free or essentially free of forms A, B, D and E of avibactam sodium as described in WO 2011/042560 A1. Preferably, the pharmaceutical composition is free or essentially free of form A of avibactam sodium.

The present invention also relates to a pharmaceutical composition comprising
(i) avibactam sodium form C as disclosed herein, preferably an effective and/or predetermined amount of avibactam sodium form C as disclosed herein, or
(ii) avibactam sodium, preferably an effective and/or predetermined amount of avibactam sodium, wherein said avibactam sodium is present as avibactam sodium form C as disclosed herein,
and optionally one or more antibacterial agents, wherein preferably at least one antibacterial agent is a beta-lactam antibiotic.

The invention further relates to a process for the preparation of avibactam sodium form C as defined herein, the process comprising a crystallization by adding a solvent containing 2-butanol and/or isobutanol into an aqueous solution of avibactam sodium, followed by at least partially removing the water, preferably by means of azeotropic distillation.

The invention also relates to a method of treating bacterial infections in humans or animals comprising administering an effective and/or predetermined amount of avibactam sodium form C as defined herein and at least one antibacterial agent, preferably a beta-lactam antibiotic.

The invention also relates to a pharmaceutical composition or medicament comprising avibactam sodium form C as defined herein for use in the treatment of bacterial infections in humans or animals.

Due to its physical form stability, avibactam sodium form C of the present invention can be used in the preparation of mixtures comprising avibactam sodium form C and at least one other physical form of avibactam sodium, preferably at least one or more anhydrous crystalline forms, e.g. crystalline form D and/or crystalline form B, and/or one or more hydrated forms, e.g. crystalline form A and/or crystalline form E, and/or amorphous avibactam sodium. Hence, the present invention also contemplates an avibactam sodium preparation and a pharmaceutical composition comprising it, wherein the avibactam sodium preparation is a mixture of a predetermined amount of polymorphic form C as described herein and at least one other physical form of avibactam sodium, preferably selected from the group consisting of anhydrous crystalline forms, e.g. crystalline form D and crystalline form B, hydrated crystalline forms, e.g. crystalline form A and crystalline form E, and amorphous avibactam sodium, and their use in a method of treating bacterial infections in humans or animals.

Definitions

As used herein the term "room temperature" refers to a temperature in the range of from 15 to 35° C., preferably of from 20 to 30° C.

As used herein, the term "amorphous" is used for non-crystalline material which lacks long-range inter-molecular order.

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material which lacks long-range order and only displays short-range order (also see explanation above), thus resulting in broad scattering. According to literature, long-range order e.g. extends over approximately $10^3$ to $10^{20}$ atoms, whereas short-range order is over a few atoms only (see "*Fundamentals of Powder Diffraction and Structural Characterization of Materials*" by Vitalij K. Pecharsky and Peter Y. Zavalij, Kluwer Academic Publishers, 2003, page 3).

The term "essentially the same" with reference to PXRD means that variabilities in peak positions and relative intensities of the peaks are to be taken into account. For example, a typical precision of the 2-Theta values is in the range of ±0.2° 2-Theta. Thus, a diffraction peak that usually appears at 6.5° 2-Theta for example can appear between 6.3° and 6.7° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only.

The term "form A" as used herein refers to the crystalline monohydrate of avibactam sodium disclosed in WO 2011/042560 A1 which is characterized by having a PXRD comprising reflections at 2-Theta angles of (8.5±0.2°), (16.4±0.2°), (17.1±0.2°), when measured at room temperature with Cu-Kalpha$_{1,2}$ radiation having a wavelength of 0.15419 nm.

As used herein, the terms "essentially pure" or "substantially pure" or "substantially polymorphically pure" with reference to crystalline form C of avibactam sodium means that, in this specific embodiment, form C includes less than about 20%, preferably less than about 10%, more preferably less than about 5%, even more preferably less than about 3% and most preferably less than about 1% by weight of any other physical form of avibactam sodium.

The term "physical form" as used herein refers to any crystalline and amorphous phase of avibactam sodium.

A "predetermined amount" of avibactam sodium form C as used herein refers to the amount of avibactam sodium form C which is present in a composition, e.g. a pharmaceutical composition, at the time of preparing said composition.

The term "effective amount" of avibactam sodium form C as used herein means an amount of avibactam sodium form C which is sufficient for protecting beta-lactam antibiotics from degradation by beta lactamase enzymes and is therefore able to maintain the antibacterial activity of beta-lactam antibiotics.

The term "about" as used herein means within 5%, more typically within 1% and most typically within 0.5% of the indicated value or range.

As used herein, the term "mother liquor" refers to the solution remaining after crystallization of a solid.

The term "treating bacterial infections" as used herein includes the cure, prevention and/or amelioration of conditions directly or indirectly caused by bacteria, in particular beta-lactamase producing bacteria.

DETAILED DESCRIPTION OF THE INVENTION

The invention is described below in further detail by embodiments, without being limited thereto.

A subject matter of the present invention is a crystalline form C of avibactam sodium.

Form C may be characterized by analytical methods well known in the field of the pharmaceutical industry for characterizing solids. Such methods comprise but are not limited to powder X-ray diffraction (PXRD), Fourier transform infrared (FTIR) spectroscopy, differential scanning calorimetry (DSC), thermogravimetric analysis (TGA) and gravimetric moisture sorption (GMS). Form C may be characterized by one of the aforementioned methods or by combining two or more of them. In particular, form C may be characterized by one of the following embodiments or by combining two or more of the following embodiments.

Crystalline form C of avibactam sodium is characterized by having a powder X-ray diffractogram comprising reflections at 2-Theta angles of (6.5±0.2°), (14.4±0.2°), (15.5±0.2°), (18.0±0.2°) and (19.3±0.2°), when measured at room temperature with Cu-Kalpha$_{1,2}$ radiation having a wavelength of 0.15419 nm.

Figure 1:
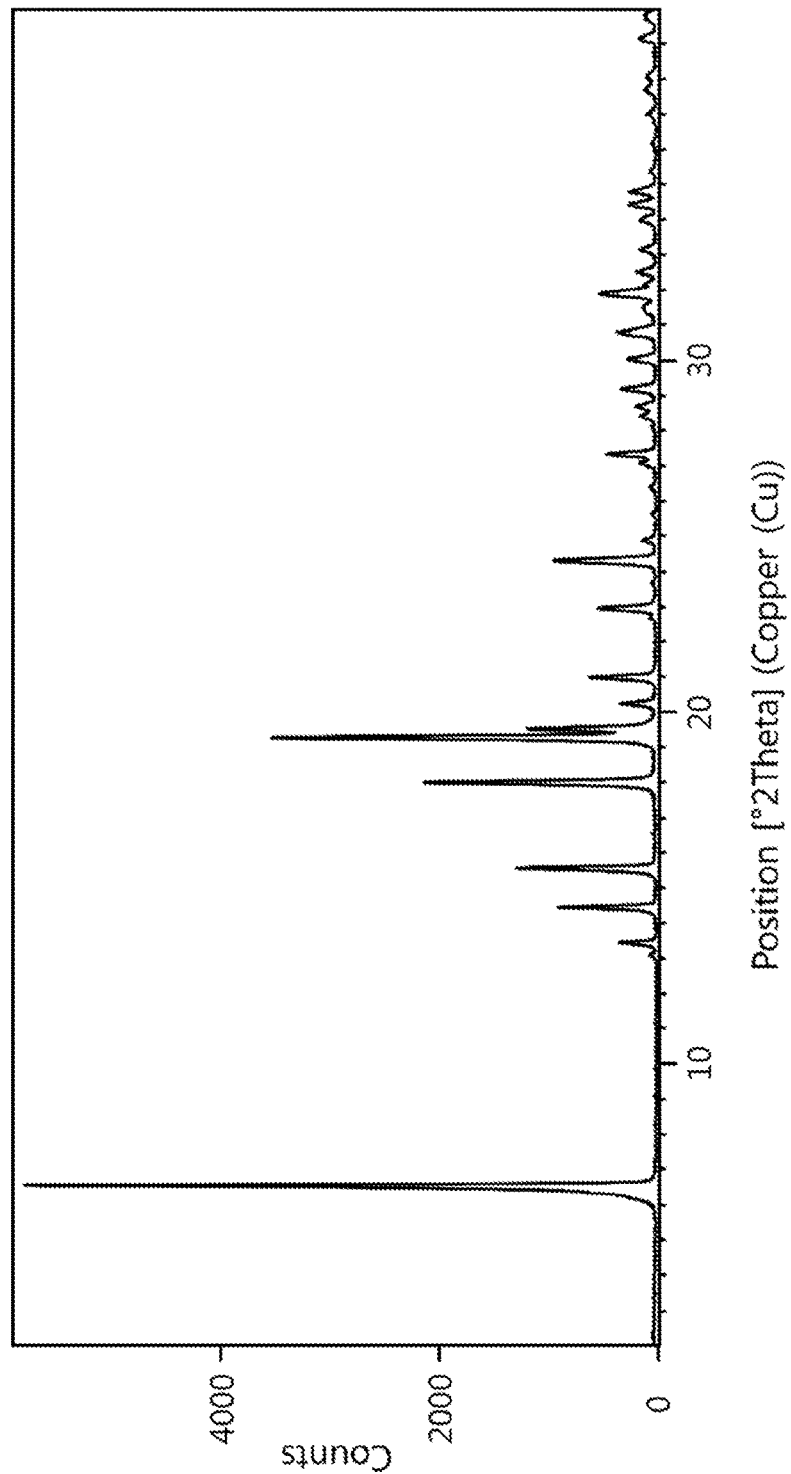
FIG. 1: Representative powder X-ray diffractogram of form C of avibactam sodium prepared according to example 1 herein

Alternatively, crystalline form C of avibactam sodium is characterized by having a powder X-ray diffractogram essentially the same as displayed in FIG. 1 of the present invention, when measured at room temperature with Cu-Kalpha$_{1,2}$ radiation having a wavelength of 0.15419 nm.

Alternatively or additionally, crystalline form C of avibactam sodium is characterized by having a Fourier transform infrared spectrum comprising peaks at wavenumbers of (3459±2) cm$^{-1}$, (1690±2) cm$^{-1}$, (1287±2) cm$^{-1}$, (1247±2) cm$^{-1}$ and (690±2) cm$^{-1}$, when measured at room temperature with a diamond ATR cell.

Alternatively or additionally, crystalline form C of avibactam sodium is characterized by having a differential scanning calorimetric curve showing a sole exothermic peak with an onset temperature of about 227° C., when measured at a temperature in the range of from 25 to 250° C. at a heating rate of 10 K/min.

Alternatively or additionally, crystalline form C of avibactam sodium is characterized by showing a weight loss of about 0.5% or less based on the weight of crystalline form C, when measured with thermogravimetric analysis at a temperature in the range of from about 25 to 200° C. and a heating rate of about 10 K/min.

As can be seen from thermal analysis crystalline form C of avibactam is highly stable against temperature stress. For example the differential scanning calorimetry curve shows no thermal events until decomposition starts at a temperature of about 227° C. and the TGA curve shows only a weight loss of about 0.5% up to a temperature of about 200° C.

Alternatively or additionally, crystalline form C of avibactam sodium is characterized by showing a weight change of not more than 0.5%, based on the weight of crystalline form C, when measured with gravimetric moisture sorption at a relative humidity in the range of form 0 to 60% and a temperature of (25.0±0.1) ° C.

According to gravimetric moisture sorption, avibactam sodium form C, when present in substantially pure polymorphic form, is stable when subjected to atmospheres having a relative humidity up to 60%. Only above this critical value form C starts to transform to the hydrated form A. Hence, in a preferred embodiment, the present invention relates to crystalline form C of avibactam sodium in substantially pure form, i.e. in a form free or substantially free of any other physical form of avibactam sodium, e.g. free or substantially free of physical forms A, B, D and/or E as described in WO 2011/042560 A1, in particular free of form A of WO 2011/042560 A1.

In particular, the invention relates to substantially pure crystalline form C of avibactam sodium including less than about 20%, preferably less than about 10%, more preferably less than about 5%, even more preferably less than about 3% and most preferably less than about 1% by weight of any other physical form of avibactam sodium.

Preferably, the present invention relates to substantially pure crystalline form C of avibactam sodium including less than about 20%, preferably less than about 10%, more preferably less than about 5%, even more preferably less than about 3% and most preferably less than about 1% by weight of crystalline form A of avibactam sodium.

More preferably, the present invention relates to substantially pure crystalline form C of avibactam sodium having a powder X-ray diffractogram comprising reflections at 2-Theta angles of (6.5±0.2°), (14.4±0.2°), (15.5±0.2°), (18.0±0.2°), (19.3±0.2°) and comprising no reflections at 2-Theta angles of about (8.5±0.2°), (16.4±0.2°) and/or (17.1±0.2°), when measured at room temperature with Cu-Kalpha$_{1,2}$ radiation having a wavelength of 0.15419 nm.

Most preferably, the present invention relates to substantially pure crystalline form C of avibactam sodium having a powder X-ray diffractogram comprising reflections at 2-Theta angles of (6.5±0.2°), (14.4±0.2°), (15.5±0.2°), (18.0±0.2°), (19.3±0.2°) and comprising no reflections at 2-Theta angles in the range of from (6.9±0.2°) to (12.6±0.2°), when measured at room temperature with Cu-Kalpha$_{1,2}$ radiation having a wavelength of 0.15419 nm.

Alternatively, the present invention relates to substantially pure crystalline form C of avibactam sodium characterized by having a powder X-ray diffractogram essentially the same as displayed in FIG. 1 of the present invention, when measured at room temperature with Cu-Kalpha$_{1,2}$ radiation having a wavelength of 0.15419 nm.

Alternatively or additionally, the invention relates to substantially pure crystalline form C of avibactam sodium characterized by having a Fourier transform infrared spectrum comprising peaks at wavenumbers of (3459±2) cm$^{-1}$, (1690±2) cm$^{-1}$, (1287±2) cm$^{-1}$, (1247±2) cm$^{-1}$, (690±2) cm$^{-1}$ and comprising no peak at wavenumbers in the range of from (3500±2) cm$^{-1}$ to (4000±2) cm$^{-1}$, preferably comprising no peaks at wavenumbers in the range of from (3463±2) cm$^{-1}$ to (4000±2) cm$^{-1}$, when measured at room temperature with a diamond ATR cell.

Alternatively or additionally, the invention relates to substantially pure form C of avibactam sodium characterized by having a differential scanning calorimetric curve showing a single exothermic peak with an onset temperature of about 227° C., when measured at a temperature in the range of from 25 to 250° C. at a heating rate of 10 K/min.

Alternatively or additionally, the invention relates to substantially pure form C of avibactam sodium characterized by showing a weight loss of about 0.5% or less, when measured with thermogravimetric analysis at a temperature in the range of from about 25 to 200° C. and a heating rate of about 10 K/min.

Alternatively or additionally, the invention relates to substantially pure form C of avibactam sodium characterized by showing a weight change of not more than 0.5%, based on the weight of crystalline form C, when measured at a relative humidity in the range of form 0 to 60% and a temperature of (25.0±0.1) ° C.

According to WO 2011/042560 A1 the therein mentioned form C mixture converts to the monohydrate form A at a relative humidity as low as 5% (page 15, lines 26 to 27).

The inventors of the present invention investigated the physical stability of crystalline form C of the present invention by way of stressing it at room temperature and various relative humidities (see also example 3 herein). It was surprisingly found that crystalline form C, in contrast to the teaching of WO 2011/042560 A1, in particular when present as polymorphically pure material, does not transform into any other physical form of avibactam sodium, when stressed at relative humidities of about 55% or below. For example, form C material remains stable after stressing it at room temperature and 55% relative humidity for 9 days and at room temperature and 45% relative humidity for 277 days and therefore shows a similar stability as form B. This behavior was confirmed by a gravimetric moisture sorption experiment performed with form C according to the present invention. According to gravimetric moisture sorption, form C shows no significant interaction with water vapor up to a relative humidity of about 60%. Above this critical value form C starts to take up water which goes along with a transformation to the monohydrate form A. Therefore, form C shows similar stability against moisture as form B, which is absolutely surprising in view of the teaching provided in WO 2011/042560 A1.

Hence, additionally or alternatively to the definitions above, form C of the present invention is characterized as having an equilibrium relative humidity of about 55% or less, preferably of about 50% or less, preferably of about 40% or less, more preferably of about 30% or less, even more preferably of about 20% or less and most preferably of about 10% or less e.g. of about 5% or less, when measured at about room temperature.

In a further aspect the present invention refers to a closed containment comprising crystalline form C of avibactam sodium as defined herein characterized by having an equilibrium relative humidity of about 55% or less, preferably of about 50% or less, preferably of about 40% or less, more preferably of about 30% or less, even more preferably of about 20% or less and most preferably of about 10% or less e.g. of about 5% or less, when measured at about room temperature.

The equilibrium relative humidity of the containment may be adjusted by purging the containment with a dry gas prior to filling or by adding a drying agent. Preferably, the containment is purged with nitrogen before avibactam sodium form C and optionally an antibacterial agent such as a beta lactam antibiotic are filled into the containment. After purging and filling the containment is closed, preferably hermetically closed.

WO 2011/042560 A1 mentions only a mixture of form C with other forms such as form A in an undefined ratio (page 3, lines 6 to 7 and page 12, lines 3 to 7). In contrast thereto, the inventors of the present invention have found a way to reliably obtain form C, and in particular to obtain form C in substantially pure polymorphic form.

Hence, a further subject matter of the present invention is a process for the preparation of crystalline form C of avibactam sodium, preferably of substantially pure form C of avibactam sodium, comprising:
  (i) providing a solution comprising avibactam sodium and water;
  (ii) mixing the solution obtained in (i) with a solvent containing 2-butanol and/or isobutanol;
  (iii) at least partially removing water from the mixture obtained in (ii);
  (iv) optionally seeding the mixture obtained in (iii) with form C crystals, preferably substantially pure form C crystals of avibactam sodium;
  (v) optionally separating at least a part of the crystals obtained in (iii) or (iv) from the mother liquor;
  (vi) optionally washing the isolated crystals obtained in (v);
  (vii) optionally drying the crystals obtained in any one of steps (iii) to (vi).

In a first step, an aqueous solution of avibactam sodium is prepared. Any physical form of avibactam sodium may be applied, for example crystalline avibactam sodium, amorphous avibactam sodium or mixtures thereof. Suitable crystalline forms, which may be used are for example forms A, B, D and E of WO 2011/042560 A1 or mixtures thereof. These crystalline forms may be prepared according to the teachings of WO 2011/042560 A1.

Avibactam sodium is dissolved in a solvent comprising water, preferably in water at a concentration in the range of from about 20 to 150 g/L, preferably from about 40 to 120 g/L and most preferably from about 60 to 100 g/L. The obtained solution may optionally be filtered in order to remove any undissolved particles. Preferably, the solution is prepared at room temperature.

Thereafter, the obtained aqueous solution is mixed with an organic solvent comprising 2-butanol, isobutanol or mixtures thereof, preferably the aqueous solution is mixed with 2-butanol, most preferably with isobutanol. The water/organic solvent ratio of the biphasic mixture is preferably in the range of from about 1:0.5 to 3, more preferably of from about 1:1 to 2.

Subsequently, the water is at least partially removed, preferably the water is removed and most preferably the water is completely removed by heating the biphasic mixture to about reflux temperature under stirring. Most preferably, the water is removed by azeotropic distillation.

Seed crystals of form C may be added to promote crystallization. Seeding may be employed to control growth of form C or to control the particle size distribution of the crystalline product.

The obtained form C crystals may optionally be collected by any conventional method such as filtration or centrifugation, most preferably by filtration.

Optionally, the isolated crystals obtained in (v) may be washed with a solvent. Preferably, the solvent comprises a water-immiscible organic solvent. Most preferably, the water-immiscible organic solvent is selected from 2-butanol, isobutanol, or mixtures thereof.

Finally, form C crystals may optionally be dried at a temperature of about 100° C. or less, preferably of about 80° C. or less, more preferably of about 60° C. or less and most preferably the crystals are dried at a temperature of about 40° C. or less for example at about room temperature. Drying may be performed for a period in the range of from about 1 to 72 hours, preferably from about 2 to 48 hours, more preferably from about 4 to 24 hours and most preferably from about 6 to 18 hours. Drying may be performed at ambient pressure and/or under vacuum preferably at about 100 mbar or less, more preferably at about 50 mbar or less and most preferably at about 30 mbar or less, for example at about 20 mbar or less.

The above described process reliably produces form C in polymorphically pure form because form C is selectively obtained from 2-butanol and/or isobutanol. The robustness of this process is advantageous compared to the process for form B production disclosed in WO 2011/042560 A1.

Surprisingly, form C of the present invention, in particular form C as obtained or obtainable by the processes as described above, was found to be physically stable against moisture and temperature stress, which qualifies it to be used for the preparation of pharmaceutical compositions.

Hence, an additional subject-matter of the present invention is the use of the crystalline form C of avibactam sodium as defined herein for the preparation of a pharmaceutical composition. Preferably, the present invention relates to the use of a substantially pure crystalline form C of avibactam sodium for the preparation of a pharmaceutical composition.

According to the invention the pharmaceutical composition of the invention can be prepared by a process comprising mixing avibactam sodium form C as defined herein and optionally other active ingredients including other polymorphic forms than form C of avibactam sodium and/or other salts or solvates of avibactam, optionally together with excipients. In case of a solid dosage form like for example a tablet, the mixture can be further processed, e.g. by pressing it so as to form the solid dosage form. Due to the physical stability of form C of the invention, all the process steps can be performed at ambient conditions.

A further subject-matter of the present invention is a pharmaceutical composition comprising crystalline form C of avibactam sodium as defined herein, preferably an effective and/or predetermined amount of crystalline form C of avibactam sodium as defined herein. Preferably, the present invention relates to a pharmaceutical composition comprising polymorphically pure or substantially polymorphically pure crystalline form C of avibactam sodium, more preferably an effective and/or predetermined amount of polymorphically pure or substantially polymorphically pure crystalline form C of avibactam sodium. In particular it is preferred that the pharmaceutical composition contains an effective amount of avibactam sodium, wherein said avibactam sodium is present as avibactam sodium form C and the pharmaceutical composition is free or substantially free of any other physical form of avibactam sodium.

The present invention further relates to a composition, preferably a pharmaceutical composition, comprising a mixture of two or more physical forms of avibactam sodium, wherein the mixture consists of a predetermined amount of avibactam sodium form C as defined herein and at least one other physical form of avibactam sodium, preferably at least one other anhydrous crystalline form, e.g. crystalline form D and/or crystalline form B, and/or one or more hydrated crystalline form(s), e.g. crystalline form A and/or crystalline form D, and/or avibactam sodium in amorphous form. For example, the invention contemplates compositions, preferably pharmaceutical compositions, comprising a mixture of avibactam sodium form C and at least one other physical form of avibactam sodium, preferably at least one other anhydrous form of avibactam sodium, in a molar ratio ranging from about 99:1 to 50:50, preferably 99:1 to 65:35. The other anhydrous form is for example crystalline form D or crystalline form B.

In addition to avibactam sodium form C, the pharmaceutical composition of the invention may contain other pharmaceutically acceptable salts and/or solvates of avibactam than avibactam sodium.

Preferably, the pharmaceutical composition of the present invention contains avibactam sodium as an active ingredient in an effective amount, wherein at least 50% (w/w), preferably at least 60, 70, 80, 90, 95, 99, 99.5, 99.8, 99.9% (w/w) of the avibactam sodium is present as polymorphic form C. It is particularly preferred, that the composition is free or at least essentially free of any other physical form of avibactam sodium, e.g. free or essentially free of amorphous avibactam sodium material, and/or free or essentially free of hydrated forms of avibactam sodium like forms A and E as described in WO2011/042560 A1, and/or free or essentially free of other anhydrous forms of avibactam sodium like forms B and D as described in WO2011/042560 A1.

In a preferred aspect the pharmaceutical composition of the invention further contains one or more antibacterial agents. Preferably, at least one antibacterial agent is a beta-lactam antibiotic including penams, penems, cephems, carbacephems, oxacephems, cephamycins, penicillins such as amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin, pivampicillin, cephalosporins such as cephalothin, cephalorodine, cefaclor, cefadroxil, cefamandole, cefazoline, cephalexin, cephradine, ceftizoxime, cefmenoxime, cefmetazole, cephaloglycin, cefonicid, cefodizime, cefpirome, ceftazidime, ceftaroline, ceftaroline fosamil, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, carbapenems such as imipenem, meropenem, biapenem, panipenem and monobactams such as aztreonam and carumonam as well as salts thereof. Most preferably, the beta-lactam antibiotic is selected from ceftazidime and/or ceftarolin fosamil.

Most preferably, the pharmaceutical composition of the present invention further comprises at least one pharmaceutically acceptable excipient.

The composition of the invention can be advantageously used in a method of treatment of bacterial infections in humans or animals suffering from bacterial infections, in particular infections caused by beta-lactamase producing bacteria.

The invention also relates to the crystalline form C of avibactam sodium as defined herein or a pharmaceutical composition or medicament comprising said avibactam sodium form C for use as medicament, in particular in the treatment of bacterial infections in humans or animals.

In various embodiments, the pharmaceutical composition of the present invention comprises a crystalline form C of avibactam sodium as defined herein, preferably in essentially pure form, and one or more antibacterial agents in a weight ratio of about 1:2, 1:3, 1:4, 1:5 or 1:6.

In various embodiments, the pharmaceutical composition of the present invention is provided in a containment, e.g. in a container or a vial, to be reconstituted and diluted. In a specific embodiment, a single containment may comprise about 0.5-5.0 g, preferably about 1.0-3.0 g, more preferably about 2.0 g of an antibacterial agent, e.g. ceftazidime, ceftaroline fosamil or aztreonam, and about 0.1-1.3 g, preferably about 0.2-1.0 g, more preferably about 0.5 g of a crystalline form C of avibactam sodium as defined herein. In an especially preferred embodiment, a single containment comprises about 2.0 g of an antibacterial agent, e.g. ceftazidime, ceftaroline fosamil or aztreonam, and about 0.5 g of a crystalline form C of avibactam sodium as defined herein.

Aspects, advantageous features and preferred embodiments of the present invention are summarized in the following items:

1) Crystalline form C of avibactam sodium characterized by having a powder X-ray diffractogram comprising reflections at 2-Theta angles of (6.5±0.2°), (14.4±0.2°), (15.5±0.2°), (18.0±0.2°) and (19.3±0.2°), when measured at a temperature in the range of from 20 to 30° C. with Cu-Kalpha$_{1,2}$ radiation having a wavelength of 0.15419 nm.
2) Crystalline form C of avibactam sodium characterized by having a powder X-ray diffractogram essentially the same as displayed in FIG. 1 of the present invention, when measured at a temperature in the range of from 20 to 30° C. with Cu-Kalpha$_{1,2}$ radiation having a wavelength of 0.15419 nm.
3) The crystalline form C according to item 1 or 2 characterized by having a Fourier transform infrared spectrum comprising peaks at wavenumbers of (3459±2) cm$^{-1}$, (1690±2) cm$^{-1}$, (1287±2) cm$^{-1}$, (1247±2) cm$^{-1}$ and (690±2) cm$^{-1}$, when measured at a temperature in the range of from 20 to 30° C. with a diamond ATR cell.
4) The crystalline form C according to any one of the preceding items characterized by having a differential scanning calorimetric curve showing a sole exothermic peak with an onset temperature of about 227° C., when measured at a temperature in the range of from 25 to 250° C. at a heating rate of 10 K/min.
5) The crystalline form C according to any one of the preceding items characterized by showing a weight loss of about 0.5% or less based on the weight of crystalline form C, when measured with thermogravimetric analysis at a temperature in the range of from about 25 to 200° C. and a heating rate of about 10 K/min.
6) The crystalline form C according to item 1 having less than 20%, less than 10%, less than 5%, less than 3% or less than 1% by weight of any other physical form of avibactam sodium.
7) The crystalline form C according to item 6, wherein the other physical form is crystalline form A, wherein form A is characterized by a powder X-ray diffractogram comprising reflections at 2-Theta angles of (8.5±0.2°), (16.4±0.2°) and (17.1±0.2°), when measured at a temperature in the range of from 20 to 30° C. with Cu-Kalpha$_{1,2}$ radiation having a wavelength of 0.15419 nm.
8) The crystalline form C according to any one of items 1 to 7 comprising no reflection at 2-Theta angles of (8.5±0.2°), (16.4±0.2°) and/or (17.1±0.2°), when measured at a temperature in the range of from 20 to 30° C. with Cu-Kalpha$_{1,2}$ radiation having a wavelength of 0.15419 nm.
9) The crystalline form C according to any one of items 1 to 8 comprising no reflection at 2-Theta angles in the range of from (6.9±0.2°) to (12.6±0.2°), when measured at a temperature in the range of from 20 to 30° C. with Cu-Kalpha$_{1,2}$ radiation having a wavelength of 0.15419 nm.
10) The crystalline form C according to any one of items 6 to 9 characterized by having a powder X-ray diffractogram essentially the same as displayed in FIG. 1 of the present invention, when measured at room temperature with Cu-Kalpha$_{1,2}$ radiation having a wavelength of 0.15419 nm.
11) The crystalline form C according to any one of items 1 to 10 characterized by having a Fourier transform infrared spectrum comprising peaks at wavenumbers of (3459±2) cm$^{-1}$, (1690±2) cm$^{-1}$, (1287±2) cm$^{-1}$, (1247±2) cm$^{-1}$, (690±2) cm$^{-1}$ and comprising no peak at wavenumbers in the range of from (3500±2) cm$^{-1}$ to (4000±2) cm$^{-1}$, when measured at a temperature in the range of from 20 to 30° C. with a diamond ATR cell.
12) The crystalline form C according to any one of items 1 to 10 characterized by having a Fourier transform infrared spectrum comprising peaks at wavenumbers of (3459±2) cm$^{-1}$, (1690±2) cm$^{-1}$, (1287±2) cm$^{-1}$, (1247±2) cm$^{-1}$, (690±2) cm$^{-1}$ and comprising no peak at wavenumbers in the range of from (3463±2) cm$^{-1}$ to (4000±2) cm$^{-1}$, when measured at a temperature in the range of from 20 to 30° C. with a diamond ATR cell.
13) The crystalline form C according to any one of items 6 to 12 characterized by having a differential scanning calorimetric curve showing a single exothermic peak with an onset temperature of about 227° C., when measured at a temperature in the range of from 25 to 250° C. at a heating rate of 10 K/min.
14) The crystalline form C according to any one of items 6 to 13 characterized by showing a weight loss of about 0.5% or less, when measured with thermogravimetric analysis at a temperature in the range of from about 25 to 200° C. and a heating rate of about 10 K/min.
15) The crystalline form C according to any one of the preceding items having an equilibrium relative humidity of about 55% or less, when measured at a temperature in the range of from 20 to 30° C.
16) The crystalline form C according to any one of the preceding items having an equilibrium relative humidity of about 50% or less, when measured at a temperature in the range of from 20 to 30° C.

17) The crystalline form C according to any one of the preceding items having an equilibrium relative humidity of about 40% or less, when measured at a temperature in the range of from 20 to 30° C.
18) The crystalline form C according to any one of the preceding items having an equilibrium relative humidity of about 30% or less, when measured at a temperature in the range of from 20 to 30° C.
19) The crystalline form C according to any one of the preceding items having an equilibrium relative humidity of about 20% or less, when measured at a temperature in the range of from 20 to 30° C.
20) The crystalline form C according to any one of the preceding items having an equilibrium relative humidity of about 5% or less, when measured at a temperature in the range of from 20 to 30° C.
21) A process for the preparation of the crystalline form C as defined in any one of the preceding items comprising:
   (i) providing a solution comprising avibactam sodium and water;
   (ii) mixing the solution obtained in (i) with a solvent containing 2-butanol and/or isobutanol;
   (iii) at least partially removing water from the mixture obtained in (ii).
22) The process according to item 21, wherein the concentration of the solution in step (i) is in the range of from 20 to 150 g/L.
23) The process according to item 21, wherein the concentration of the solution in step (i) is in the range of from 40 to 120 g/L.
24) The process according to item 21, wherein the concentration of the solution in step (i) is in the range of from 60 to 100 g/L.
25) The process according to any one of items 21 to 24, wherein the solution in step (i) is filtered.
26) The process according to any one of items 21 to 25, wherein the solution in step (i) is prepared at a temperature in the range of from 20 to 30° C.
27) The process according to any one of items 21 to 26, wherein in step (ii) the solution obtained in step (i) is mixed with 2-butanol, isobutanol or mixtures thereof
28) The process according to item 27, wherein in step (ii) the solution obtained in step (i) is mixed with 2-butanol.
29) The process according to item 27, wherein in step (ii) the solution obtained in step (i) is mixed with isobutanol.
30) The process according to any one of items 21 to 29, wherein the water/organic solvent ratio is in the range of from 1:0.5 to 3.
31) The process according to item 30, wherein the water/organic solvent ratio is in the range of from 1:1 to 2.
32) The process according to any one of items 21 to 31, wherein in step (iii) the water is removed from the mixture obtained in step (ii).
33) The process according to item 32, wherein in step (iii) the water is completely removed from the mixture obtained in step (ii).
34) The process according to any one of items 21 to 33, wherein the water is partially removed, removed or completely removed by heating the biphasic mixture obtained in step (ii) to reflux temperature under stirring.
35) The process according to any one of items 21 to 33, wherein the water is partially removed, removed or completely removed by azeotropic distillation.
36) The process according to any one of items 21 to 35 further comprising step (iv) seeding the mixture obtained in step (iii) with form C crystals of avibactam sodium according to any one of items 1 to 20.
37) The process according to any one of items 21 to 36 further comprising step (v) separating at least a part of the crystals obtained in step (iii) or (iv) from the mother liquor.
38) The process according to item 37, wherein the crystals are collected by filtration or centrifugation.
39) The process according to item 38, wherein the crystals are collected by filtration.
40) The process according to any one of items 37 to 39 further comprising step (vi) washing the isolated crystals with a solvent.
41) The process according to item 40, wherein the solvent comprises a water-immiscible organic solvent.
42) The process according to item 41, wherein the water-immiscible organic solvent is 2-butanol.
43) The process according to item 41, wherein the water-immiscible organic solvent is isobutanol.
44) The process according to item 41, wherein the water-immiscible organic solvent is a mixture of 2-butanol and isobutanol.
45) The process according to any one of items 21 to 44 further comprising step (vii) drying the crystals.
46) The process according to item 45, wherein the crystals are dried at a temperature of 100° C. or less.
47) The process according to item 45, wherein the crystals are dried at a temperature of 80° C. or less.
48) The process according to item 45, wherein the crystals are dried at a temperature of 60° C. or less.
49) The process according to item 45, wherein the crystals are dried at a temperature of 40° C. or less.
50) The process according to item 45, wherein the crystals are dried at a temperature in the range of from 20 to 30° C.
51) The process according to any one of items 45 to 50, wherein drying is performed for a period in the range of from 1 to 72 hours.
52) The process according to any one of items 45 to 50, wherein drying is performed for a period in the range of from 2 to 48 hours.
53) The process according to any one of items 45 to 50, wherein drying is performed for a period in the range of from 4 to 24 hours.
54) The process according to any one of items 45 to 50, wherein drying is performed for a period in the range of from 6 to 18 hours.
55) The process according to any one of items 45 to 54, wherein drying is performed at ambient pressure.
56) The process according to any one of items 45 to 54, wherein drying is performed under vacuum at 100 mbar or less.
57) The process according to any one of items 45 to 54, wherein drying is performed under vacuum at 50 mbar or less.
58) The process according to any one of items 45 to 54, wherein drying is performed under vacuum at 30 mbar or less.
59) The process according to any one of items 45 to 54, wherein drying is performed under vacuum at 20 mbar or less.
60) Use of the crystalline form C as defined in any one of items 1 to 20 for the preparation of a pharmaceutical composition.

61) A pharmaceutical composition comprising an effective and/or predetermined amount of crystalline form C as defined in any one of items 1 to 20 and optionally one or more antibacterial agents.
62) A pharmaceutical composition comprising an effective amount of avibactam sodium and optionally other pharmaceutically acceptable salts and/or solvates of avibactam, wherein avibactam sodium is present in crystalline form C as defined in any one of items 1 to 20, and further optionally one or more antibacterial agents.
63) A pharmaceutical composition comprising avibactam sodium, wherein avibactam sodium is present as a mixture of two or more physical forms of avibactam sodium, wherein the mixture consists of a predetermined amount of avibactam sodium form C as defined in any one of items 1 to 20 and at least one other physical form of avibactam sodium, and optionally one or more antibacterial agents.
64) The pharmaceutical composition according to item 63, wherein at least one other physical form of avibactam sodium is an anhydrous crystalline form and/or amorphous form.
65) The pharmaceutical composition according to item 63 or 64, wherein the molar ratio of the predetermined amount of avibactam sodium form C and at least one other physical form of avibactam sodium in the mixture is between 99:1 and 50:50.
66) The pharmaceutical composition according to items 61 to 65, wherein the one or more antibacterial agents are selected from ceftazidime and/or ceftarolin fosamil.
67) The pharmaceutical composition according to items 61 to 66 further comprising at least one pharmaceutically acceptable excipient.
68) The pharmaceutical composition as defined in any one of items 61 to 67 for use as medicament.
69) The pharmaceutical composition as defined in any one of items 61 to 68 for use in the treatment and/or prevention of bacterial infections.

The following non-limiting examples are illustrative for the disclosure and shall not limit the scope of the invention.

EXAMPLES

Powder X-ray diffraction (PXRD) was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-Theta with 40 s per step (255 channels) in the angular range of 2° to 40° 2-Theta at ambient conditions. A typical precision of the 2-Theta values is in the range of ±0.2° 2-Theta. Thus, the diffraction peak of substantially pure form C that appears for example at 6.5° 2-Theta can appear between 6.3 and 6.7° 2-Theta on most X-ray diffractometers under standard conditions.

Fourier transform infrared spectroscopy (FTIR) was performed with a MKII Golden Gate™ Single Reflection Diamond ATR (attenuated total reflection) cell with a Bruker Tensor 27 FTIR spectrometer with 4 cm$^{-1}$ resolution at ambient conditions. To record a spectrum a spatula tip of the sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, the infrared peak of substantially pure form C that appears at 3459 cm$^{-1}$ can appear between 3457 and 1761 cm$^{-1}$ on most infrared spectrometers under standard conditions.

DSC was performed on a Mettler Polymer DSC R instrument. The sample was heated in a 40 microL aluminum pan with pierced aluminum lid from 25 to 250° C. at a rate of 10 K/min. Nitrogen (purge rate 50 mL/min) was used as purge gas.

TGA was performed on a Mettler TGA/DSC 1 instrument. The sample was heated in a 100 microL aluminum pan closed with an aluminum lid. The lid was automatically pierced at the beginning of the measurement. The sample was heated from 25 to 200° C. at a rate of 10 K/min. Nitrogen (purge rate 50 mL/min) was used as purge gas.

Moisture sorption isotherms were recorded with an SPSx-1μ moisture sorption analyzer (ProUmid, Ulm). The measurement cycle was started at ambient relative humidity (RH) of 30% and first decreased to 3% RH and then to 0% RH. Afterwards RH was increased from 0% to 80% in a sorption cycle and decreased to 0% in a desorption cycle in 5% steps and finally increased to 30% RH in one step. The time per step was set to a minimum of 2 hours and a maximum of 6 hours. If an equilibrium condition with a constant mass of ±0.01% within 1 hour was reached before the maximum time for all examined samples the sequential humidity step was applied before the maximum time of 6 hours. If no equilibrium was achieved the consecutive humidity step was applied after the maximum time of 6 hours. The temperature was 25±0.1° C.

Example 1: Crystalline Form C of Avibactam Sodium

Avibactam sodium (160 mg, crystalline form D e.g. prepared according to example 5 of WO 2011/042560 A1) was dissolved in 2 mL water. To the solution 3 mL isobutanol were added and the biphasic mixture was heated to a bath temperature of 119° C. to remove the water azeotropically. After water removal a precipitate occurred. The suspension was allowed to cool to room temperature, the solid was collected by filtration and sucked dry on the filter.

Yield: 98 mg (61% of theory), DSC (10 K/min): exotherm with onset temperature of 227° C., TGA (10 K/min): mass change of 0.5% by weight from about 25 to 200° C.

The powder X-ray diffractogram of the obtained material is displayed in FIG. 1 and a reflection list is provided in table 1.

TABLE 1

Reflection list and corresponding relative intensities of crystalline form C between 2.0 and 30.0° 2-Theta

| Angle [±0.2 °2-Theta] | Relative Intensity [%] |
| --- | --- |
| 6.5 | 100 |
| 13.1 | 1 |
| 13.4 | 6 |
| 14.4 | 16 |
| 15.5 | 22 |
| 18.0 | 37 |
| 19.3 | 61 |
| 19.5 | 20 |
| 20.2 | 5 |
| 21.0 | 10 |
| 22.9 | 9 |

TABLE 1-continued

Reflection list and corresponding relative intensities of crystalline form C between 2.0 and 30.0° 2-Theta

| Angle [±0.2 °2-Theta] | Relative Intensity [%] |
|---|---|
| 24.3 | 15 |
| 24.9 | 2 |
| 26.4 | 1 |
| 27.0 | 2 |
| 27.3 | 8 |
| 28.4 | 2 |
| 28.7 | 3 |
| 29.2 | 6 |
| 30.0 | 4 |

Figure 2:
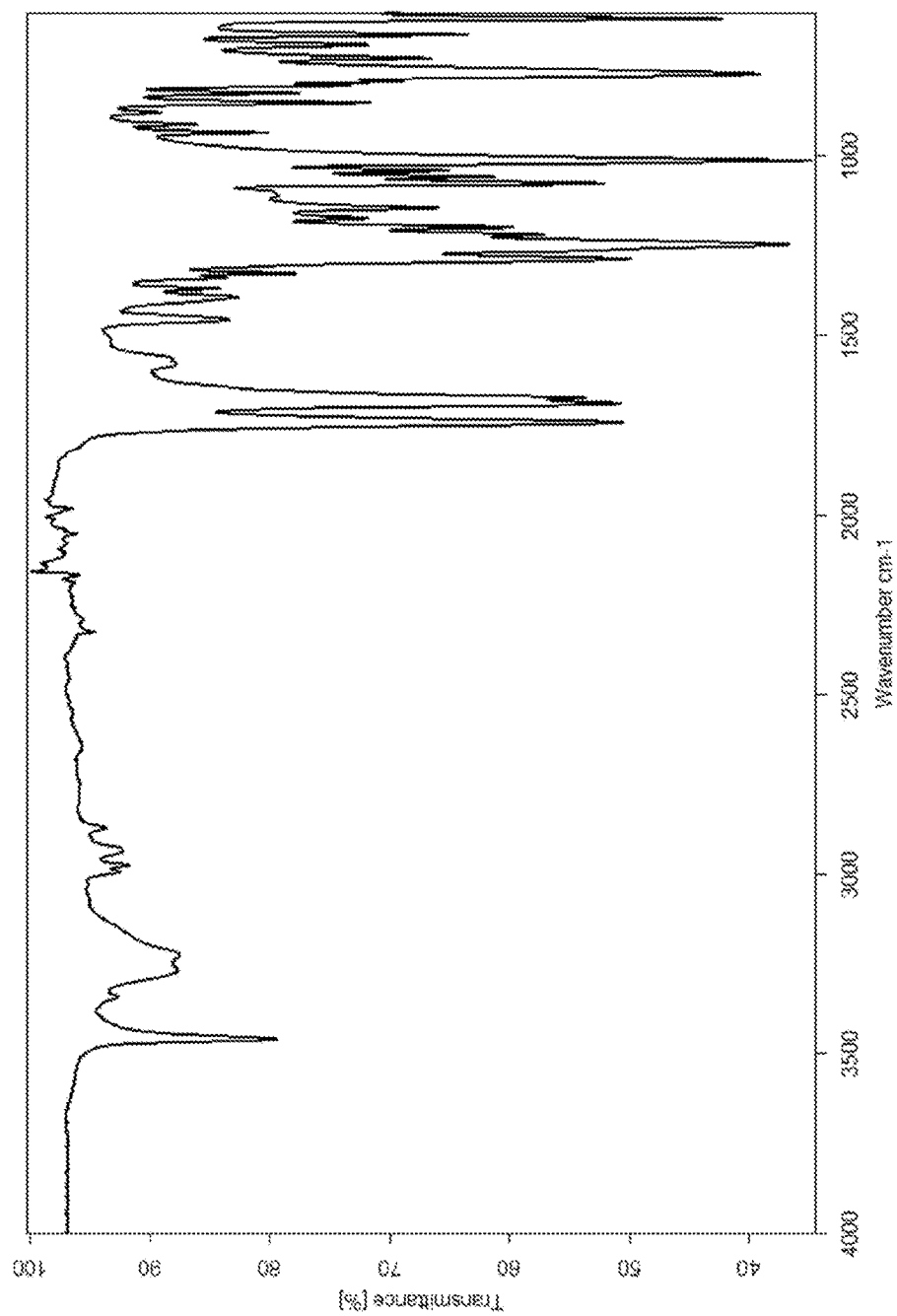
FIG. 2: Representative Fourier transform infrared spectrum of form C of avibactam sodium prepared according to example 1 herein
Figure 3:
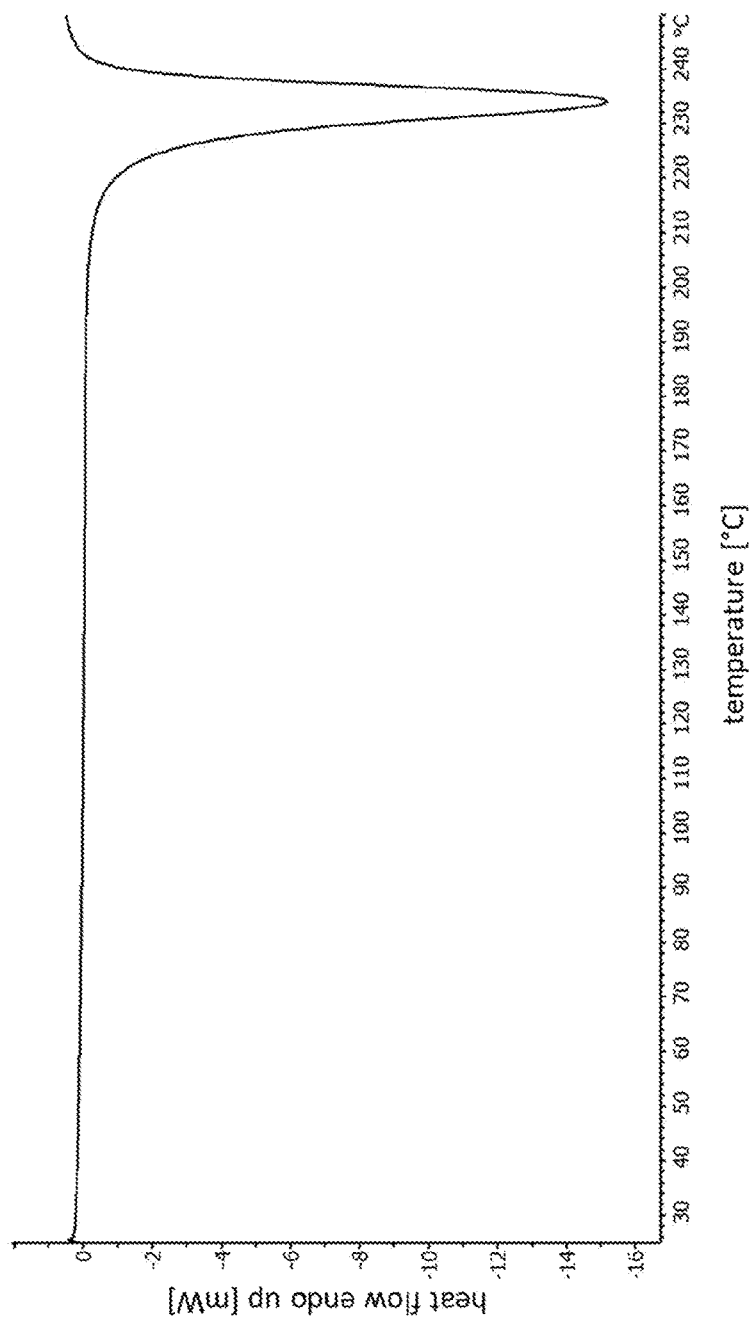
FIG. 3: Representative differential scanning calorimetric curve of form C of avibactam sodium prepared according to example 1 herein
Figure 4:
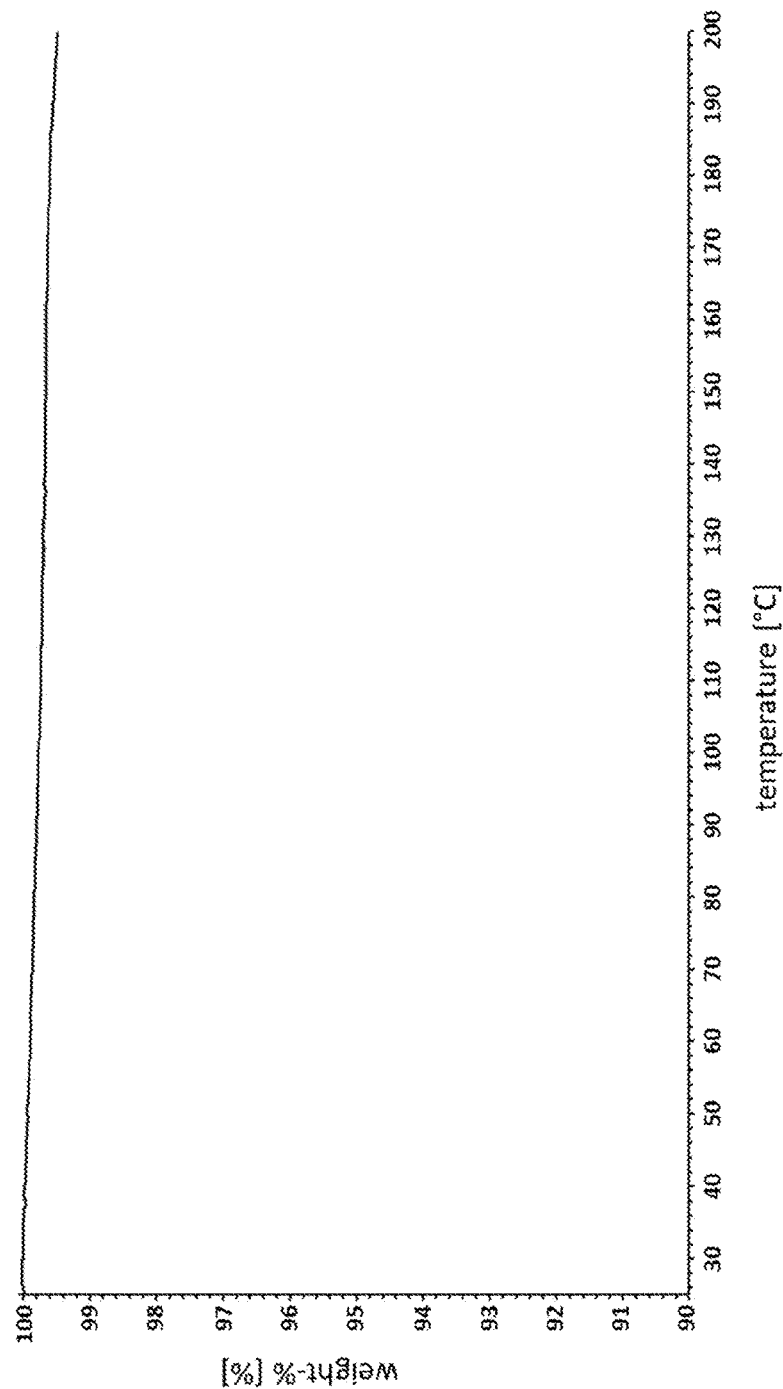
FIG. 4: Representative thermogravimetric analysis curve of form C of avibactam sodium prepared according to example 1 herein

The Fourier transform infrared spectrum of the obtained material is displayed in FIG. 2 and a peak list is provided in table 2.

TABLE 2

| FTIR peak list of crystalline form C Wavenumber [±2 cm$^{-1}$] |
|---|
| 3459 |
| 3341 |
| 3269 |
| 3224 |
| 2992 |
| 2973 |
| 2936 |
| 2870 |
| 1742 |
| 1690 |
| 1673 |
| 1577 |
| 1455 |
| 1392 |
| 1368 |
| 1339 |
| 1326 |
| 1287 |
| 1247 |
| 1219 |
| 1198 |
| 1173 |
| 1145 |
| 1077 |
| 1058 |
| 1040 |
| 1013 |
| 935 |
| 912 |
| 880 |
| 852 |
| 825 |
| 804 |
| 793 |
| 771 |
| 727 |
| 690 |
| 661 |
| 617 |

Example 2: Crystalline Form C of Avibactam Sodium

Avibactam sodium (164 mg, crystalline form D e.g. prepared according to example 5 of WO 2011/042560 A1) was dissolved in 2 mL water. To the solution 3 mL 2-butanol were added and the biphasic mixture was heated to a bath temperature of 135° C. to remove the water azeotropically. After water removal a precipitate occurred. The suspension was allowed to cool to room temperature, the solid was collected by filtration and sucked dry on the filter. Powder X-ray diffraction confirmed the receipt of crystalline form C. Yield: 102 mg (62% of theory), Example 3: Stress Tests Crystalline form C (prepared according to example 1 herein) was open stored at room temperature in desiccators over saturated salt solutions generating different relative humidities. The samples were analyzed by powder X-ray diffraction and the results are summarized in table 2 below:

TABLE 3

Summary of stress tests performed with crystalline form C as starting material

| Relative Humidity (saturated salt solution) | Results and Comments |
|---|---|
| 45% (K$_2$CO$_3$) | substantially pure form C after 9 days and after 277 days |
| 55% (Ca(NO$_3$)$_2$ × 4H$_2$O) | substantially pure form C after 9 days |
| 63% (NaBr) | traces of form A detectable after 3 days |
| 75% (NaCl) | mainly form A with traces of form C after 3 days |
| 86% (KCl) | form A after one day |

The invention claimed is:

1. Crystalline form C of avibactam sodium having a powder X-ray diffractogram comprising reflections at 2-Theta angles of (6.5±0.2°), (14.4±0.2°), (15.5±0.2°), (18.0±0.2°) and (19.3±0.2°), when measured at a temperature in the range of from 20 to 30° C. with Cu-Kalpha$_{1,2}$ radiation having a wavelength of 0.15419 nm.

2. The crystalline form C of claim 1 having less than 20% by weight of any other physical form of avibactam sodium.

3. The crystalline form C of claim 1 comprising no reflection at 2-Theta angles of (8.5±0.2°), (16.4±0.2°) and/or (17.1±0.2°), and/or comprising no reflection at 2-Theta angles in the range of from (6.9±0.2°) to (12.6±0.2°), when measured at a temperature in the range of from 20 to 30° C. with Cu-Kalpha$_{1,2}$ radiation having a wavelength of 0.15419 nm.

4. The crystalline form C according to claim 1 characterized by having
   (i) a Fourier transform infrared spectrum comprising peaks at wavenumbers of (3459±2) cm$^{-1}$, (1690±2) cm$^{-1}$, (1287±2) cm$^{-1}$, (1247±2) cm$^{-1}$ and (690±2) cm$^{-1}$, when measured at a temperature in the range of from 20 to 30° C. with a diamond ATR cell, and/or
   (ii) an equilibrium relative humidity of about 55% or less, when measured at a temperature in the range of from 20 to 30° C.

5. A composition comprising
   (i) crystalline form C of avibactam sodium as defined in claim 1 and
   (ii) one or more additional physical form(s) of avibactam sodium which is not the crystalline form C as defined in claim 1.

6. The composition of claim 5, wherein the molar ratio of the crystalline form C and the one or more additional physical form(s) of avibactam sodium is in the range of from 99:1 to 50:50.

7. The composition of claim 5, wherein the one or more additional physical form(s) of avibactam sodium is selected from the group consisting of an anhydrous crystalline form, a hydrated crystalline form and/or amorphous avibactam sodium.

8. A process for the preparation of the crystalline form C of avibactam sodium as defined in claim 1 comprising:
   (i) providing a solution comprising avibactam sodium and water;
   (ii) mixing the solution obtained in (i) with a solvent containing 2-butanol and/or isobutanol;
   (iii) at least partially removing water from the mixture obtained in (ii).

9. Crystalline form C of avibactam sodium obtainable or obtained by the process according to claim 8.

10. A pharmaceutical composition comprising:
   (i) crystalline form C of avibactam sodium as defined in claim 1;
   (ii) optionally one or more antibacterial agent(s);
   (iii) optionally one or more pharmaceutically acceptable excipient(s).

11. The pharmaceutical composition according to claim 10, wherein the one or more antibacterial agent(s) is a beta-lactam antibiotic.

12. The pharmaceutical composition according to claim 11, wherein the beta-lactam antibiotic is selected from the group consisting of ceftazidime, ceftaroline fosamil and aztreonam.

13. A method of treating bacterial infections in humans or animals, caused by beta-lactamase producing bacteria, comprising administering an effective and/or predetermined amount of avibactam sodium form C as defined in claim 1 and at least one antibacterial agent.

* * * * *